United States Patent [19]

Klein

[11] Patent Number: 5,052,999
[45] Date of Patent: Oct. 1, 1991

[54] LIPOSUCTION METHOD AND APPARATUS

[76] Inventor: Jeffrey A. Klein, 203 Calle Conchita, San Clemente, Calif. 92672

[21] Appl. No.: 471,417

[22] Filed: Jan. 29, 1990

[51] Int. Cl.$^5$ ............................................. A61N 1/30
[52] U.S. Cl. ...................................... 604/19; 604/49; 604/73; 604/119; 128/758
[58] Field of Search .................. 604/19, 73, 93, 118, 604/119, 121, 129, 317, 319; 128/758

[56] References Cited

U.S. PATENT DOCUMENTS

| | | |
|---|---|---|
| 844,410 | 2/1907 | Schauer . |
| 2,715,899 | 8/1955 | MacLean ............................ 128/758 |
| 3,071,402 | 1/1963 | Lasto et al. . |
| 3,208,145 | 9/1965 | Turner . |
| 3,438,607 | 4/1969 | Williams et al. . |
| 3,804,089 | 4/1974 | Bridgman . |
| 3,807,401 | 4/1974 | Riggle et al. . |
| 3,828,780 | 8/1974 | Morrison, Jr. . |
| 3,902,494 | 9/1975 | Haberlen et al. . |
| 4,221,220 | 9/1980 | Hansen ................................ 604/119 |
| 4,299,221 | 11/1981 | Phillips et al. . |
| 4,536,180 | 8/1985 | Johnson . |
| 4,617,013 | 10/1986 | Betz . |
| 4,627,444 | 12/1986 | Brooker ............................ 128/758 |
| 4,753,634 | 6/1988 | Johnson .............................. 604/73 |
| 4,834,703 | 5/1989 | Dubiul et al. ....................... 604/48 |
| 4,857,047 | 8/1989 | Amoils ............................... 604/119 |

Primary Examiner—Stephen C. Pellegrino
Assistant Examiner—Michael Rafa
Attorney, Agent, or Firm—Knobbe, Martens, Olson & Bear

[57] ABSTRACT

An improved liposuction handle incorporates a vacuum control for regulating the amount of suction applied during the liposuction procedure. An alternative embodiment allows for sequential performance of both the step of administering anesthetic to the surgical area and performing the liposuction procedure by the same instrument, the device additionally allowing for sterile collection of cells and tissue. Additionally, an improved liposuction method is disclosed, particularly suited for performance under local anesthesia.

4 Claims, 2 Drawing Sheets

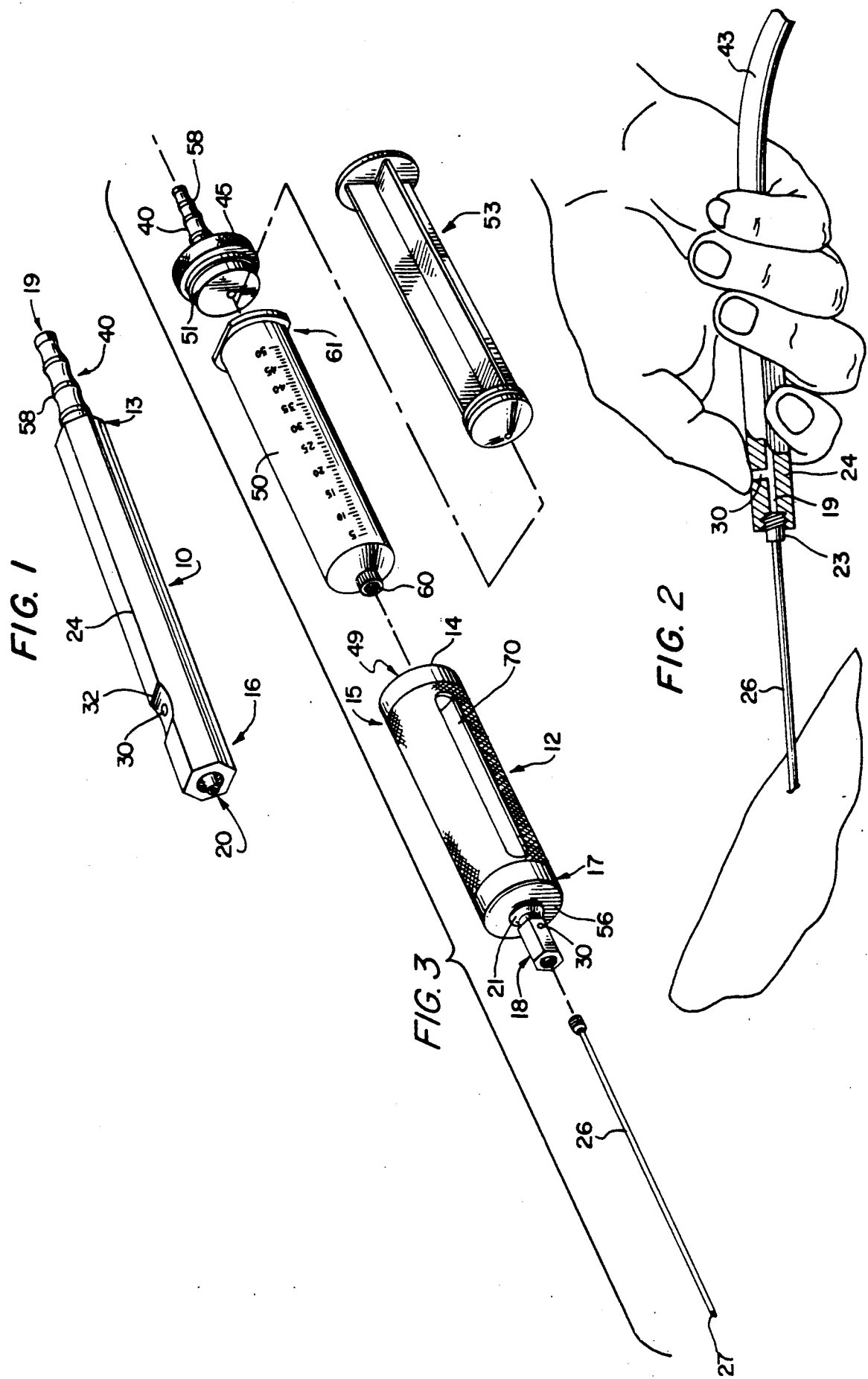

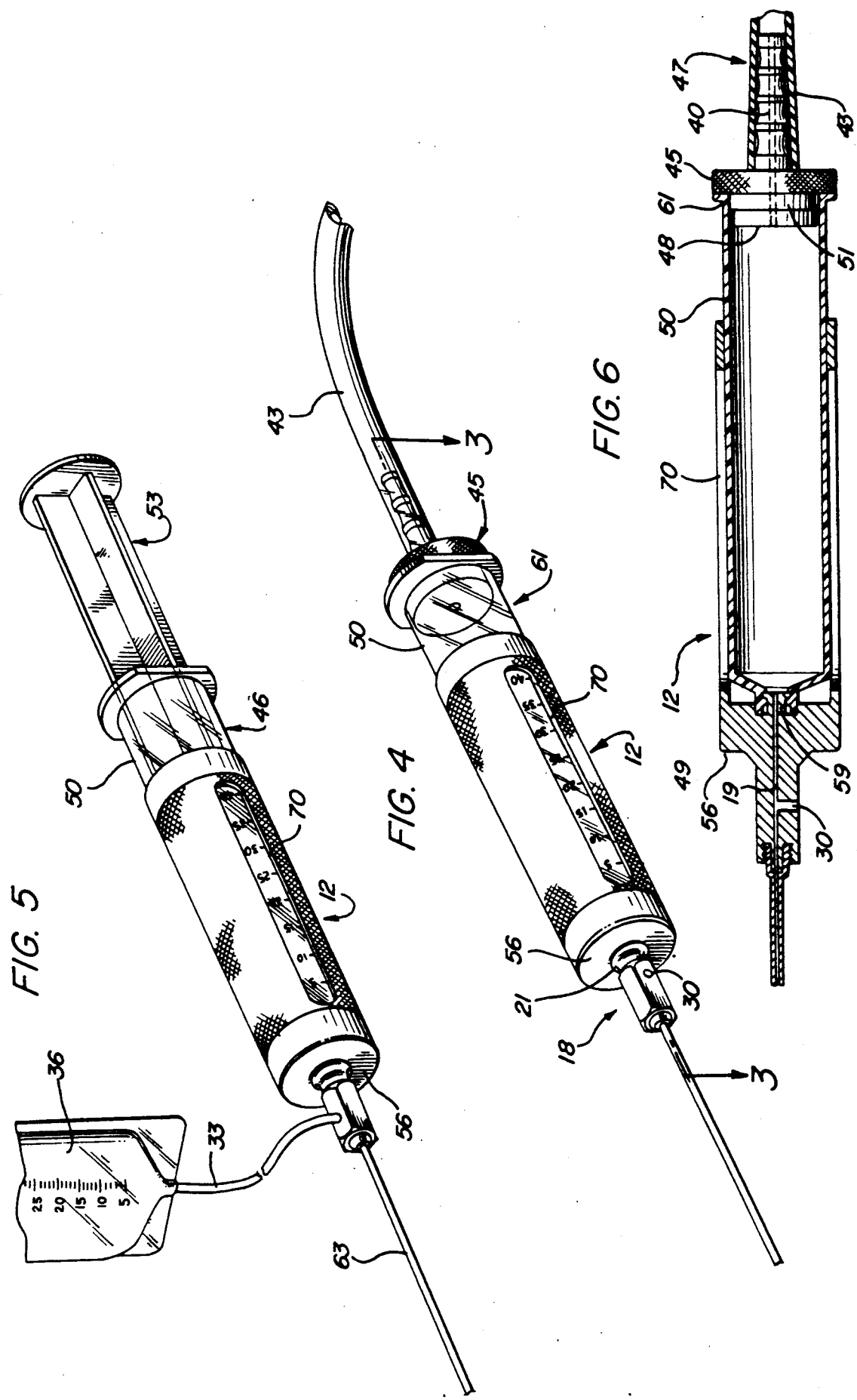

LIPOSUCTION METHOD AND APPARATUS

BACKGROUND OF THE INVENTION

The present invention relates generally to the field of surgical instruments. More specifically, the present invention relates to an improved liposuction apparatus and method for removing excess subcutaneous fat deposits from various areas of the body.

Body fat varies in structure and composition in different regions of the body. Much of the subcutaneous fat in a normal, healthy human is generally arranged to form a thin blanket-like layer. In some areas of the body fat cells exist in large subcutaneous deposits. Adipose tissue consists of fat cells and fibrous tissue. Fat cells store lipids. Any variety of metabolic disorders or dietary habits can cause fat deposits to become excessively enlarged, with undesirable cosmetic and medical sequelae.

Liposuction is an invasive surgical procedure where subcutaneous fat cells are removed by the use of a liposuction cannula attached to a vacuum suction device. The cannula is percutaneously inserted into subcutaneous deposits of fat through very small (4 mm to 10 mm) incisions. As the cannula is carefully advanced, fat cells are dislodged by the force of the applied vacuum and simultaneously suctioned away via a long flexible hose connecting the cannula to the vacuum pump collection bottle.

Anesthesia for liposuction surgery can be accomplished in a number of ways, including general anesthesia, regional spinal anesthesia, local anesthesia with either deep IV sedation or nitrous oxide sedation, as well as simple infiltration local anesthesia without either IV sedation or narcotic analgesia. Liposuction is usually accomplished using general anesthesia. During general anesthesia, the patient's breathing is maintained by means of endotracheal intubation and respiratory ventilation machine. Risks for morbidity and mortality associated with general anesthesia are related to problems of maintaining adequate oxygenation. Local anesthesia is safer than general anesthesia because the patient is awake and breathing naturally without assistance.

Liposuction by local anesthesia requires the subcutaneous infiltration of a local anesthetic agent prior to the insertion of the liposuction cannula. With careful and methodical injection, and subsequent limited diffusion of the anesthetic within the adjacent fatty tissues, large areas of subcutaneous fat can be profoundly anesthetized.

Conventional liposuction techniques which are performed under local anesthesia generally use a syringe and needle for administering the anesthetic, with a separate apparatus then performing the liposuction procedure. The procedure thereby requires that a variety of syringes, needles and surgical instruments be introduced into the sterile field to separately provide anesthesia and perform the liposuction procedure.

In addition, conventional liposuction devices are generally designed for use with full suction produced by the vacuum source. If it is necessary to control the strength of the suction applied during the liposuction procedure, the user must generally either remove the cannula from the patient, thus necessitating its reinsertion which increases localized trauma, or reduce suction at the source of the vacuum. These alternatives increase the risk of infection due to cannula withdrawal and reinsertion, and also require complex or inconvenient remote control of the vacuum source away from the site of the procedure.

The cells and tissue harvested from the patient's body during a liposuction procedure are typically discarded. Conventional liposuction apparatus and techniques do not conveniently provide for the sterile collection and reuse of such material for other purposes, such as performing fat biopsies or repositioning the collected material in other areas of the body. Use of suctioned fat for these purposes necessitates its maintenance in a sterile environment to reduce the chance of contamination and requires that cells be handled in such a way to minimize damage to the cells.

Thus, there remains a need for a vacuum device which enables a simple, sterile process for administering anesthesia and performing liposuction procedures, and controlling the suction through the device. Another object of the invention is to provide a liposuction handle device having the above-mentioned advantages, in addition to the advantage of allowing sterile collection and reinsertion or analysis of harvested cells without undue manipulation or environmental exposure of the collected cells.

SUMMARY OF THE INVENTION

Briefly, the present invention comprises a multiple-function handle device to be used in conjunction with liposuction procedures.

In a first embodiment, referred to as a KLEIN MICROCANNULA HANDLE TM type liposuction device, is a tubular liposuction handle device having a proximal end and a distal end is provided. Preferably, the tubular handle is provided with a luer connector disposed at the distal end for receiving the standard luer connector of a liposuction cannula. A vacuum hose attachment is provided at the proximal end of the handle to allow attachment of the handle to a vacuum source. A continuous internal lumen runs axially throughout the interior of the handle, connector and vacuum attachment, the lumen of a diameter sufficient to allow the passage of fat cells and other subcutaneous tissues therethrough.

The handle is further provided with a vacuum control, which is in the form of a vent extending through the wall of the handle and into the lumen. The external surface of the handle surrounding the vent is preferably recessed to allow the user's thumb to readily locate and seal or open the vent, thereby controlling the degree of vacuum in the cannula. The vacuum control vent in the handle device allows the user to continue to run the vacuum source throughout the procedure, yet provides a convenient method of discontinuing or controlling the vacuum flow when needed.

In a second embodiment, a medical vacuum device is provided which allows both the administration of a local anesthetic agent and also the performance of the liposuction procedure under continuously controllable vacuum conditions. In addition, the device is adapted to selectively permit the sterile collection of fat cells harvested from the liposuction procedure for subsequent re-injection elsewhere within the patient's body.

In the second embodiment, referred to as a KLEIN SYRINGE HANDLE TM type liposuction device, the handle of the device is provided with a syringe housing, the housing adapted to receive a syringe through an open proximal end thereof, with the conventional luer connector of the syringe fitting into a corresponding luer connector located at the distal interior end of the syringe housing. In this manner, the interior of the syringe is placed in communication with the liposuction cannula. The syringe housing is preferably provided with one or more viewing windows, extending along opposite sides thereof, through which the user may observe the level of material contained within the syringe.

Disposed at the outer distal end of the handle and in fluid communication with the syringe is a male luer connector adapted to receive a standard anesthetic administering needle or liposuction cannula. Also in communication with the syringe is a vacuum control comprising a vent drilled through an outer wall of the handle into the lumen connecting the syringe connector to the cannula connector.

A detachable vacuum connector, referred to as a KLEIN CORK TM type connector, is adapted to be inserted into the proximal end of the syringe body, providing air-tight communication between the syringe body and the vacuum source to provide a vacuum to the apparatus.

In accordance with the method of the present invention, a medical vacuum device is provided substantially in the form of the first described embodiment of the device of the present invention. Following administration of an anesthetic agent, the liposuction cannula is percutaneously inserted into the patient and located within the appropriate subcutaneous region. The vacuum source is activated and the vent is partially or fully occluded by the user's finger to commence the liposuction procedure. After a sufficient volume of material has been drawn through the vacuum device, the cannula is removed from the patient and the vacuum source is disengaged.

In accordance with another embodiment of the method of the present invention, a syringe handle is provided which is substantially in the form of the second described embodiment of the apparatus of the present invention. A syringe is inserted into the chamber in the syringe housing and an anesthetic solution reservoir is placed in fluid communication with the lumen of the handle by way of the vent extending through the handle into the lumen.

An anesthetic administering needle is secured to the distal end of the handle device and the needle is percutaneously inserted into the patient in the area to be anesthetized. The syringe plunger is withdrawn, thus causing a selected amount of medicinal fluid to flow from the anesthetic solution reservoir and be collected in the syringe body. The flow from the anesthetic solution source is then discontinued, and the anesthetic solution is expressed from the syringe body through the lumen of the handle and anesthesia needle connected to the distal end of the syringe handle into a selected subcutaneous tissue area. Preferably, reverse flow of fluid back into the reservoir is minimized by clamping the line connecting the reservoir to the vent. The steps of collecting and applying the anesthetic solution to the subcutaneous area may be repeated a number of times until the desired amount has been delivered.

After the anesthetic has been administered, the IV line that connected the anesthetic solution source to the syringe handle is then withdrawn from the vent, and the plunger is withdrawn from the syringe. A KLEIN CORK (vacuum connector) is inserted into the open proximal en ..of the syringe body, providing air-tight communication between the syringe body and a vacuum source to provide a vacuum to the apparatus. The anesthetic needle is removed from the distal end of the device and a liposuction cannula secured in its place. Suction is then applied to the needle through the syringe body via the vacuum connector to remove subcutaneous tissue through the lumen of the handle. The vacuum control vent can be used to regulate the liposuction vacuum, as described in connection with the prior embodiment.

Material which has been removed from the patient is collected within the syringe body, which may be replaced by additional empty syringe bodies as needed. The collected material is thereafter available for analysis or for repositioning within the patient.

In accordance with a further aspect of the method of the present invention, there is provided a method for the removal of fatty material from a subcutaneous zone in a subject mammal, which comprises the steps of subcutaneously infiltrating a sufficient volume of fluid within the subcutaneous zone to substantially increase the tumescence of the fatty material contained therein, thereby facilitating manual control of a vacuum cannula within the subcutaneous zone. At least a portion of the tumescent fatty material is there after removed from the zone using a vacuum cannula. The fluid comprises a dilute anesthetic solution of lidocaine having a concentration of approximately 0.1% to 0.05% lidocaine. Preferably, the anesthetic solution further comprises sodium bicarbonate (12.5 meq/L) and epinephrine (1:1,000,000).

Further features and advantages of the present invention will be understood from the Detailed Description of Preferred Embodiments which follows, when considered together with the drawings and the claims.

BRIEF DESCRIPTION OF THE DRAWINGS

FIG. 1 is a perspective view of a first embodiment of the KLEIN MICRO-CANNULA HANDLE TM of the present invention.

FIG. 2 is a partial sectional view of the KLEIN MICRO-CANNULA HANDLE TM of FIG. 1, depicting the handle in use.

FIG. 3 is an exploded perspective view of the components of a second embodiment of the liposuction handle of the present invention.

FIG. 4 is a perspective view of the assembled components, as depicted in FIG. 3, in the vacuum mode.

FIG. 5 is an alternative assembled view of the components depicted in FIG. 3, in the anesthetic administration mode.

FIG. 6 is an elevational sectional view along line 6—6 of FIG. 4.

DETAILED DESCRIPTION OF THE PREFERRED EMBODIMENTS

Referring now to the drawings, there is shown in FIG. 1 a first embodiment of an improved liposuction handle embodying the present invention.

The handle 10 comprises an elongate tubular wall 24 having a proximal end 13, a distal end 16, and a longitudinal lumen 19 running axially throughout the length of the handle. The lumen 19 is preferably of a diameter sufficient to allow the passage of cells and other subcutaneous material therethrough, and is most preferably from about 2 to 5 mm in diameter. Although the lumen 19 can have any of a variety of cross-sectional configurations, it is for manufacturing simplicity preferably provided with a circular cross-section.

The distal end 16 of the handle terminates in a connector 20. The connector 20 is adapted to removably receive appropriate needles or cannula used during the liposuction procedure. Connector 20 preferably comprises a standard male luer lock connector adapted to connect with standard female luer connector 23 on a conventional needle. (See FIG. 2) However, any of a variety of conventional connectors may be used in the present invention as would be apparent to one skilled in the art.

A vent 30 extends through outer wall 24 of the handle 10, preferably in the distal one-half or one-third the length of the handle 10. The vent 30 extends through wall 24 and is in communication with lumen 19. Preferably, vent 30 has a cross-sectional dimension of from about 2 mm to about 3 mm, and is preferably disposed in a shallow recess 32 (see FIG. 1). Recess 32 enables the operator to readily locate vent 30 during a liposuction procedure and facilitates a controlled partial or complete seal by the finger of the user when application of vacuum is desired.

A vacuum attachment 40 is provided at the proximal end 13 of the handle 10. Vacuum attachment 40 of the handle 10 preferably has a configuration which allows for connection to a conventional vacuum tubing 43. Thus, the vacuum attachment typically has a reduced outer diameter relative to that of the handle 10 and comprises a plurality of radially outwardly extending ridges 58, the ridges successively decreasing in diameter in the proximal direction to produce a generally frustoconical configuration as is well known for this purpose. Any conventional structure for attaching vacuum tubing 43 may be adapted for use for the attachment 40 of the handle 10, the particular configuration largely a matter of design choice.

The handle 10 is preferably shaped to comfortably rest and be secured in the user's hand, to facilitate controlled manipulation of the handle 10 during the liposuction procedure. For instance, the handle may have a hexagonal (see FIG. 1) or other cross-sectional configuration to provide a suitable gripping surface for the user. The handle may also be formed in the shape of a gun grip or other non-linear form to improve the user's grip. A wide variety of alternative configurations or surface textures of the outer wall 24 of the handle 10 may also be used, as will be understood by one of skill in the art.

The handle 10 and its component parts are preferably machined or molded from a material which is corrosion-resistant and resistant to conventional methods of sterilization of surgical instruments. Preferably, the handle is machined from a metal such as brass or stainless steel; however, any of a variety of other metals known in the art capable of use in the intended environment of the present invention may also be used. Alternatively, the handle 10 can be molded or extruded from any of a variety of thermoplastic polymers, as will be well understood by one skilled in the medical devices art. In the embodiment illustrated in FIGS. 1 and 2, the handle is machined from stainless steel. Connector 20 is a separately manufactured standard male luer connector made of brass and chrome plated which is press fit into an enlarged portion of the interior lumen 19.

In a second embodiment of the present invention, illustrated in FIGS. 3-6, handle 12 is radially enlarged, to provide an interior chamber 49 extending from an area preferably proximal the vent 30 and throughout the handle to its proximal end. The chamber 49 is adapted to removably receive a reservoir such as syringe 46, which preferably comprises a conventional syringe body 50 and removable plunger 53. Any of a variety of different sized syringes can be used with the present invention, provided it can produce a relatively air-tight seal at its distal end with connector 59, which will be discussed. The use of a sterile plunger 53 and syringe body 50 in conjunction with the present invention helps to maintain the sterility of the system.

The interior surface of distal wall 56 of the chamber 49 is provided with a connector 59 for removably engaging the distal end of syringe 46. Thus, connector 59 is preferably a standard female luer lock connector which fits snugly into a conventional complementary male luer lock connector 60, such as that typically found on a conventional syringe. The connection between connectors 59 and 60 provides fluid communication between the lumen 19 of the handle 12 and the interior of syringe body 50.

The connector 59 on the interior of chamber 49 can be integrally formed within syringe housing 56. Alternatively, the connector 59 can be separately manufactured and then secured to the interior surface of distal wall 56 of chamber 49 by welding or other processes known in the art to be suitable for the materials from which the wall 56 and connector 59 are constructed.

As illustrated in FIGS. 3-6, one or more longitudinally extending windows 70 are preferably provided along the sides of the syringe housing 49, allowing the user to observe the level of fluid or other material collected in the syringe 46.

A vacuum connector 45 is adapted to sealingly fit into the proximal end 61 of the syringe body 50 to provide communication between the interior of the syringe body 50 and vacuum tubing 43. Thus, distal end 48 of the vacuum connector 45 is provided with an axially extending annular surface 51 configured to fit snugly within the proximal end 61 of the syringe body 50. The outer radius of the annular surface 51 is approximately equal to the inner radius of the proximal end 61 of the syringe body 50, to provide a friction fit which produces an air and water-tight seal between the syringe body 50 and the vacuum connector 45.

The proximal end 47 of the vacuum connector 45 is provided with a standard vacuum attachment 40 for receiving vacuum tubing 43. The vacuum attachment 40 comprises a plurality of radially outwardly extending ridges 58, decreasing in outer diameter toward the proximal end 47 of the vacuum attachment 40. The configuration of the rings 58 provides a secure air and water-tight connection between the vacuum attachment 40 and the vacuum tubing 43.

The liposuction handle 12 in accordance with the present embodiment may be readily manufactured by techniques well known to one of skill in the art. For example, referring to FIG. 3, it is seen that most of the length of handle 12 is made up of a substantially cylindrical body having an opening 14 at the proximal end 15 thereof. The distal end 17 of the tubular body is provided with a distal wall 56.

The tubular body is conveniently milled from a suitable metal as has been discussed or can be molded or extruded from any of a variety of appropriate polymeric materials. In a preferred embodiment, distal wall 56 is machined from round stainless steel stock, and is welded onto the distal end 17 of a stainless steel tubular body.

Distal wall 56 is provided with an opening into which a manifold portion 18 is secured. Preferably, manifold portion 18 is secured to distal wall 56 by means of an annular weld 21. Manifold portion 18 is provided with an axially extending lumen 19 therethrough, to enable fluid communication between the interior of syringe 46 and cannula 26, as has been discussed. Thus, manifold portion 18 is provided with vent 30, such as by drilling a female luer connector, to permit both regulation of the vacuum and connection of a source of an anesthetic agent, as will be discussed in connection with the method of the present invention.

The distal end of manifold portion 18 is provided with a male luer lock connector 20 for receiving a standard needle cannula 26. The male luer lock connector 20 can be machined directly onto the manifold portion 18. Preferably, however, the distal end of manifold portion 18 is provided with a radially enlarged bore, into which a preformed luer connector 20 is inserted and secured, such as by welding or friction fit.

The vacuum connector 45 is conveniently manufactured by milling on a lathe. Both the outer flange of the vacuum connector 45 and the handle 12 are preferably provided with a high friction surface, such as a knurled cross hatch pattern, which can be conveniently milled into the surface by known techniques. Window 70 in the side of handle 12 may be produced by stamping or cutting techniques known in the art.

In accordance with the method of the present invention, the handle 10 of FIGS. 1 and 2 is connected to a vacuum source (not shown) by way of a flexible vacuum tubing 43 attached to the vacuum connector 40. Any of a variety of conventionally known vacuum sources may also be used with the present invention, such as will be known to one of skill in the art.

The patient is then anesthetized either by administration of a general anesthetic or by localized injection, as appropriate for the particular procedure and patient. A liposuction cannula 26 of appropriate size is selected and secured to connector 20, and the liposuction cannula 26 is thereafter inserted percutaneously, preferably through a small incision.

An important feature of the present invention is the ability of the user to control the suction applied to the cannula 26 while performing the liposuction procedure. When the vacuum is applied to the handle 10 with the vent 30 uncovered, air is drawn through the vent 30 into the lumen 19. Air bleeding into the lumen 19 through the vent 30 tracks proximally through the lumen 19 of the handle 10 to the vacuum source, thereby reducing or effectively eliminating any vacuum at distal opening 27 of liposuction cannula 26. With the vent 30 in an open position, little, if any, material will be drawn through the distal opening 27 of the cannula 26.

When the user desires to remove subcutaneous material, the vent 30 is partially or fully occluded, preferably by placing a finger over the vent 30 until the desired degree of suction is achieved. Thus, adjusting finger pressure over the vent 30 of the handle 10 controllably varies the amount of air drawn through the vent 30 into the lumen 19. Thus, the strength of the suction at the distal opening 27 of the liposuction cannula can be conveniently regulated without reducing or controlling the vacuum at its source.

In an alternative method of the invention, which may be accomplished using the embodiment of the device illustrated in FIGS. 3-6, a needle 63 for administering a local anesthetic is first attached to the connector 20 at the distal end 17 of the handle 12.

A syringe 46 having a tubular body 50 and plunger 53 are inserted into the proximal end of the chamber 49. When the syringe body 50 is advanced axially towards the connector 59 on distal wall 56, the syringe body 50 is automatically guided by the inner walls of the chamber 49. The male luer lock connector 60 of the syringe 46 is coupled with the corresponding female luer lock connector 59 on wall 56 of the syringe chamber 49 to provide an air and water-tight seal. Although the dimension of the handle 12 and of the syringe 46 can be varied for liposuction procedures of different magnitudes, the inventor has found the use of a standard 60 cc syringe and correspondingly dimensioned handle 12 to be suitable under most circumstances.

A standard flexible IV line 33 connected to a fluid reservoir 36 is then connected to vent 30 of the handle, thus providing fluid communication between the fluid reservoir 36 and the lumen 19 of the handle 12. The fluid reservoir 36 is preferably adapted to hold medicinal fluids, preferably a suitable anesthetic solution, such as dilute lidocaine in normal saline, preferably along with a suitable vasoconstrictor, such as epinephrine.

The ratios of anesthetic and vasoconstricting solutions can be varied considerably, as is well known to one of skill in the art. In one preferred solution, 500 mg of lidocaine and 1 mg of epinephrine are mixed with 1,000 ml saline. Depending on the size of the area to be anesthetized, and the strength of the anesthetic, the total volume of anesthetic solution dispensed in a given procedure may also vary widely and is within the judgment of one skilled in the art.

The connection between line 33 and vent 30 can be a simple friction fit. Any of a variety of conventional interlocking structures such as a luer connector may be readily adapted for securing line 33 in fluid communication with vent 30.

When plunger 53 of the syringe 46 is drawn in a proximal direction, anesthetic flows from the fluid reservoir 36 through the flexible line 33 and into syringe body 50 by way of vent 30 and lumen 19. This is accomplished with the distal end of the anesthetic needle partially or fully occluded, such as by a needle cap or by insertion beneath the skin.

After the syringe body 50 is filled with the desired volume of anesthetic, and prior to administration of the anesthetic, the IV line 33 is preferably occluded to prevent reverse flow out of vent 30 and back into the reservoir 36. This may be accomplished, for example, by simply kinking the line 33 or through the use of a standard compression clamp on IV line 33 as are well known in the art, or preferably by use of an in-line one-way check-valve in IV line 33.

The use of an in-line check-valve enables anesthetic to be delivered without the need to disconnect line 33 from vent 30 in order to prevent reverse flow.

Next, the administration of the anesthetic agent is performed. The tip of the needle 63 is located in the area of the subcutaneous layer of tissue to be removed and the anesthetic agent is administered by pushing plunger 53 distally into the syringe body 50. This action transfers the anesthetic from the syringe body 50, out the tip of the anesthetic needle 63.

The steps of transferring anesthetic from the reservoir 36 to the syringe and administering the anesthetic may be repeated by "pumping" the plunger 53 as many times as necessary in order to adequately anesthetize the desired area. This process is particularly simplified by use of the in-line check-valve in IV line 33 which permits free flow from the reservoir toward the handle, but blocks all retrograde flow. When the syringe has become empty, the operator need merely retract the syringe plunger 53 and draw additional anesthetic into the syringe. Although this process will theoretically also draw material into the distal end of needle 63, this has been determined in practice not to present any problem.

In this manner, the needle 63 need not be withdrawn from the tissue to replenish the anesthetic within the syringe if repeated applications of the anesthetic agent are desired. This procedure reduces the risk of infection and accelerates the process of administering the anesthetic by eliminating the steps of withdrawing and reinserting the needle within the patient and disconnecting and reconnecting the fluid source when multiple applications of anesthetic are desirable.

Following the administration of a suitable volume of anesthetic, the IV line 33 is removed from the vent 30, and the plunger 53 is removed from the proximal end of the syringe. The anesthesia administering needle 63 is then preferably withdrawn from the patient's body and detached from the handle 12 at the connector 20. Although the same needle used to subcutaneously dispense the anesthetic may also be used to withdraw material during the liposuction procedure, the liposuction cannula 26 and anesthetic administering needle 63 are preferably separate devices. Thus, an appropriately sized liposuction cannula 26 is preferably selected and connected to the connector 20 of handle 12.

The vacuum connector 45 is connected to a vacuum line 43, which is in turn connected to a vacuum source, and the annular flange portion 51 of vacuum connector 45 is snugly fit into the proximal end 61 of syringe body 50. Vacuum is applied to the handle 12, providing a suction at the vent 30 and at the opening 27 of cannula 26. During application of the vacuum, the suction reaching the opening 27 of the cannula 26 is regulated by the user by positioning a finger or thumb upon the vent 30, as described above. The liposuction technique is then performed, with movement of the liposuction needle 26 by the user to dislodge and remove subcutaneous fat and tissue. Suction created in the cannula 26 pulls the dislodged subcutaneous material through the cannula 26 and into the syringe body 50, with the user controlling suction in the device throughout the procedure.

If, in a given liposuction procedure, sufficient material is removed to more than fill the syringe body 50, the device can be readily disassembled and a new empty syringe or other reservoir inserted within the chamber 49 in handle 12. The present invention enables the convenient storage of materials removed during the liposuction procedure, within a sterile environment. Thus, the materials contained within a syringe body 50 are ready for reinjection into the patient at a different location, such as during reconstructive or other reshaping procedures, or is available for any type of diagnostic analysis appropriate for the type of material which has been removed.

Liposuction procedures performed in accordance with the present invention provide a dramatic improvement over the traditional methods that require either general anesthesia or deep IV sedation and narcosis, and are believed safer than liposuction by general anesthesia. Furthermore, the "tumescent technique" method of the present invention, detailed infra, is associated with less discomfort, allows a more rapid post-operative recovery and enables better anesthetic result than when liposuction is performed using other anesthetic techniques.

The tumescent technique in accordance with the present invention for local anesthesia permits regional local anesthesia of the skin and subcutaneous tissues by using direct infiltration rather than by using a proximal nerve block. Infiltrating large volumes of a dilute anesthetic solution consisting of lidocaine (0.1% or preferably no more than about 0.05%) and epinephrine (1:1,000,000) in physiologic saline, within a fatty tissue zone, produces swelling and firmness, or tumescence, of the targeted fatty areas.

Recent clinical studies of the absorption pharmacokinetics of lidocaine infiltrated as disclosed herein have shown that peak plasma lidocaine levels occur approximately 12 to 14 hours after beginning the infiltration. This remarkably delayed absorption permits a much higher lidocaine dosage than was previously believed possible, since any reduction in a drug's rate of systemic absorption will reduce the magnitude of the drug's peak plasma levels. The safe upper limit for lidocaine dosage using the tumescent technique has been estimated by the present inventor to be about as high as 35 mg/kg. This is approximately five times greater than recognized standard lidocaine dosage limitations. Clinical local anesthesia persists for up to 18 hours, typically obviating the need for post-operative analgesia.

Infiltrating a large volume of dilute epinephrine assures diffusion throughout the entire targeted area while minimizing any risk of tachycardia and hypertension. The associated vasoconstruction is so complete that there is virtually no blood loss with liposuction. The mechanical and pharmacologic properties of the fluid that is injected subcutaneously prevent the massive shifts of intravascular fluids which are usually seen when liposuction is done by general anesthesia. Thus, with the tumescent technique, in accordance with the present invention, there is no longer any need to replace significant volumes of IV fluids.

Infiltration of local anesthesia has traditionally been limited to relatively small areas of skin for two reasons: (1) the stinging-pain associated with infiltrating the local anesthesia is not easily tolerated, and (2) published dosage limitations have precluded anesthetizing large areas of skin. These limitations have now been overcome in view of the present inventor's discovery that (1) adding sodium bicarbonate in order to neutralize the acidity of commercially available local anesthetic solutions of lidocaine and epinephrine dramatically reduces the usual burning-stinging pain of infiltration, and (2) using dilute solutions of lidocaine with the tumescent technique permits profound anesthesia of very large areas.

A variety of significant advantages are accrued by the method and apparatus of the present invention, including a minimization of blood loss due to the liposuction procedure. The extensive vasoconstriction produced by large volumes of dilute epinephrine, preferably about 1:1,000,000, has been found to typically produce less than 12 ml of whole blood for each liter of pure fat removed by liposuction. One week following the liposuction of a liter of fat there is virtually no change in the patient's peripheral venous hematocrit.

A remarkable aspect of the technique in accordance with the present invention is the substantial absence of post-operative discomfort. Treated areas remain at least partially anesthetized for up to 18 hours after surgery. Thus, for liposuction, it is not necessary to use local anesthetics which are longer acting and more cardiotoxic than lidocaine. After liposuction by the technique disclosed herein, patients do not require analgesia postoperatively. Although some patients do take acetaminophen for soreness, narcotic analgesics are not prescribed.

Regarding the cosmetic results of the method of the present invention, the tumescent technique minimizes the risks of post-operative irregularities of the skin. With careful and methodical infiltration, the skilled clinician can produce uniform tumescence, avoiding irregularities and distortions. Magnifying or enlarging the targeted fatty components, and using smaller suction cannulas (e.g., 1.5 mm=12 gauge and 4.7 mm=3/16 inch outside diameter), permits liposuction to be done more uniformly and more completely. Because of the tumescent "magnification" of subcutaneous fat, focal residual collections of fat are more easily detected and treated before completion of the surgery. These features of the tumescent technique minimize irregularities of the skin which are more likely to be seen after liposuction when only general anesthesia is used.

Certain areas of the body have traditionally been regarded as areas where it is relatively difficult to achieve good results by liposuction. Areas which are prone to develop post-surgical irregularities of the skin or are otherwise difficult to treat by traditional liposuction methods include the medial proximal thighs, anterior thighs, upper abdomen, calves and ankles. With traditional liposuction techniques, controlling the direction of the cannula through the zones of soft jelly-like fat of the medial thighs is technically difficult. The mobility of this fatty tissue causes the cannula to travel repeatedly along the same path, predisposing to focally excessive fat removal. However, when this fatty compartment has been made firm and swollen by the infiltration method disclosed herein, smaller liposuction cannulas can easily be directed to achieve a smooth uniform fat reduction. Using the tumescent technique of the present invention, these areas are routinely treated with excellent results.

Thus, the present invention provides a significantly improved method of removing subcutaneous material, which comprises the step of subcutaneously infiltrating a sufficient volume of fluid, particularly a dilute local anesthetic, to achieve a localized anesthesia, as well as a tumescent firming of the fatty tissue. After the fatty tissue has been sufficiently swollen that its mobility is substantially reduced, the fatty tissue is removed under vacuum.

Preferably, sodium bicarbonate is added to the anesthetic solution to minimize the pain of infiltration. Prior to using sodium bicarbonate in the local anesthetic solution, the stinging-burning pain of infiltration was enough to necessitate the use of IV sedation and narcotic analgesia. This technique is a substantial and unexpected improvement over the method first published by the inventor in the Tumescent Technique for Liposuction Surgery, Am. J. Cosmetic Surg., 4:263-267, 1987. Using an even more dilute lidocaine solution, no more than 0.05% instead of 0.1%, greatly improves tumescence with better vasoconstriction and more uniform anesthesia. With the use of sodium bicarbonate (approximately 12.5 meq/L) to neutralize the pH of the anesthetic solution, the tumescent technique does not require IV sedation or narcotic analgesia.

When only one or two body areas are treated by liposuction, usually no sedation is needed. When two or more areas are treated, requiring the patient to remain recumbent for more than 2 hours, 2.5 mg to 5 mg of midazolam is given intramuscularly with a 30-gauge needle and repeated in 2 to 3 hours if necessary. Certain patients will also be given 25 mg of demerol IV just prior to beginning liposuction of the abdomen.

Because of the minimal blood loss associated with the tumescent technique and because of the large volumes of normal saline infiltrated into fat, routine IV fluid replacement is not necessary. Nevertheless, an IV is routinely established to provide access for resuscitative medications in the unlikely event of an emergency.

For liposuction totally by local anesthesia, the Klein Handle TM liposuction device (see FIGS. 3-6) is preferably used for the initial infiltration of local anesthetic. It is designed to permit the efficient subcutaneous infiltration of large volumes of a local anesthetic solution while assuring minimal discomfort in patients who are fully awake.

For this purpose, a spinal needle (20 gauge, 3.5 inches long) is optimally used first, followed by an intradiscal needle (18 gauge, 6 inches long). The 20-gauge needle is used initially because it causes less discomfort than an 18-gauge needle when passed through unanesthetized tissue. These needles are inserted at sites around the periphery of the targeted fatty compartment either through intact skin, or through the incision sites that will be used to insert the liposuction cannula. The sites of needle insertion are initially anesthetized using a 30-gauge needle on a 6 cc syringe to infiltrate a small bleb of the local anesthetic solution intradermally.

Filling a 60 cc syringe with anesthetic is the first step in using either the Klein Handle TM device of FIGS. 3-6 or Klein Needle TM liposuction devices. An IV line is attached to the IV bottle containing the anesthetic solution. Next, the IV line is connected to a 60 cc syringe, the IV line flow-regulator clamp is opened and the syringe plunger is retracted.

Inserting the 60 cc syringe into the embodiment illustrated in FIGS. 3-6, the syringe is turned until it is engaged with the luer-lock attachment. The IV line is then attached directly to the side-port 30 of the Klein Handle TM (see FIG. 5), and either a 20-gauge 3.5 inch long spinal needle or an 18-gauge 6 inch long intradiscal needle is attached to the connector 20. Finally, the needle is inserted through anesthetized skin into subcutaneous fat, and the infiltration begins.

Final stage local infiltration is accomplished using a long, e.g., 30 cm long, 4 mm outside diameter, needle which is preferably welded to a syringe handle. A blunt-tipped needle is preferred because it is less likely than a sharp needle to puncture subjacent fascia. In an awake patient, the blunt tip will cause discomfort when it encounters an area not previously well anesthetized. Upon detecting an area not adequately anesthetized, the surgeon or anesthesiologist can immediately infiltrate additional anesthetic exactly where it is needed. When testing for completeness of anesthesia, the blunt tipped needle, such as the Klein Needle TM, available from Jeff Klein Surgical, Inc., P.O. Box 1269, San Clemente, Calif. 92672, is an essential part of the tumescent technique for liposuction totally by local anesthesia.

Uniform infiltration is most easily accomplished by using a grid pattern drawn by a blue felt-tipped on the overlying skin pre-operatively. By infiltrating anesthetic solution as the needle is advanced, large volumes can be instilled quickly and uniformly, producing firm tumescence, and extensive vasoconstriction and local anesthesia.

While particular embodiments of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A method for the removal of subcutaneous material, comprising:
    providing a surgical vacuum device having a proximal end, a distal end and a central lumen extending therethrough, said proximal end comprising a container housing adapted to removably receive a container in communication with the central lumen;
    placing a remotely located anesthetic reservoir in fluid communication with the lumen, by way of a vent extending through the wall of said device and into the lumen;
    removably securing a container within the container housing;
    drawing a selected amount of anesthetic from the reservoir into said container through said lumen;
    expressing anesthetic from said container through said lumen and into the subcutaneous material; and
    thereafter connecting a vacuum cannula in communication with the lumen and applying a vacuum to the lumen to remove subcutaneous material through the vacuum cannula.

2. The method of claim 1, wherein the container is a plunger activated syringe body.

3. The method of claim 2, wherein said step of applying a vacuum is performed by connecting a vacuum source to said syringe body.

4. The method of claim 3, wherein said step of applying a vacuum comprises connecting said vacuum source to a vacuum attachment, said attachment adapted to provide air-tight communication between said syringe body and said vacuum source.

* * * * *